(12) United States Patent
Sarokin

(10) Patent No.: US 6,368,848 B1
(45) Date of Patent: Apr. 9, 2002

(54) COMPOSITIONS TO IDENTIFY PLANT PROTEINS THAT FUNCTION IN G-PROTEIN COUPLED SYSTEMS

(75) Inventor: Laura Patricia Sarokin, Skillman, NJ (US)

(73) Assignee: BASF Aktiengesellschaft (DE)

( * ) Notice: Subject to any disclaimer, the term of this patent is extended or adjusted under 35 U.S.C. 154(b) by 0 days.

(21) Appl. No.: 09/393,007

(22) Filed: Sep. 9, 1999

Related U.S. Application Data

(62) Division of application No. 08/801,980, filed on Feb. 19, 1997, now Pat. No. 5,985,584.

(51) Int. Cl.[7] .............................. C12N 1/19; C12N 1/21; C12N 15/63
(52) U.S. Cl. ............................... 435/254.11; 435/252.3; 435/419; 435/325; 435/320.1
(58) Field of Search .............................. 435/320.1, 325, 435/419, 252.3, 254.11

(56) References Cited

U.S. PATENT DOCUMENTS 5,079,163 A * 1/1992 Piatak, Jr. et al.
5,985,584 A * 11/1999 Sarokin

FOREIGN PATENT DOCUMENTS

| WO | WO 95/02823 | 1/1995 |
|---|---|---|
| WO | WO 97/22004 | 6/1997 |
| WO | WO 97/48820 | 12/1997 |
| WO | WO 98/00545 | 1/1998 |
| WO | WO 98/00715 | 1/1998 |

OTHER PUBLICATIONS

King et al., Oct. 1990, Science 250:121–123.*
Dietzel et al., Sep. 1987, Cell 50:1001–1010.*
Miller et al. Journal of Experimental Botany, vol. 47, No. 301, pp 983–992 (1996).
Weiss et al. PNAS USA 91:9554–9558.
Ma. Plant Mol. Biol. 26:1611–1636.
Kang et al. Mol. Cell biol. 10:2582–2590.
Kim et al. Plant Physiol. 108:1315–1316.
Ma et al. PNAS USA 87:3821–3825.
Ma et al. Gene 107:189–195.

* cited by examiner

*Primary Examiner*—Elizabeth Kemmerer
(74) *Attorney, Agent, or Firm*—Sutherland Asbill & Brennan, LLP

(57) ABSTRACT

The present invention is directed to a method of identifying plant proteins that function as or similar to G protein coupled receptors, or as plant G protein subunits utilizing a bioassay system that incorporates such plant proteins. Further aspects of the present invention provides expression vectors and yeast cells transformed therewith encoding the plant proteins whose identity it is desired to determine, and methods of utilizing same.

4 Claims, No Drawings

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

GAATTCAAAA AAATGGGCTT ACTCTGCAGT AGAAG             35

(2) INFORMATION FOR SEQ ID NO:2:

(i) SEQUENCE CHARACTERISTICS:
      (A) LENGTH: 43 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

TCGACTTCTA CTGCAGAGTA AGCCCATTTT TTGAATTCCT GCA       43

COMPOSITIONS TO IDENTIFY PLANT PROTEINS THAT FUNCTION IN G-PROTEIN COUPLED SYSTEMS

This is a divisional of application Ser. No. 08/801,980 filed on Feb. 19, 1997, now U.S. Pat. No. 5,985,584 the entire disclosure of which is hereby incorporated by reference.

FIELD OF INVENTION

This invention relates to bioassay techniques utilizing plant proteins expressed in a host cell system to identify their functionality in a plant G protein-coupled system, and is particularly useful in identifying plant G protein subunits and plant proteins that function in a manner similar to such G protein subunits and G protein coupled receptors. Other embodiments of the invention relate to host cells expressing such plant proteins, and especially plant G protein subunits, vectors useful for making such cells, and methods of making and using same.

BACKGROUND OF THE INVENTION

In animal systems, the actions of many extracellular signals, for example: neurotransmitters, hormones, odorants and light, are mediated by receptors with seven transmembrane domains (G protein-coupled receptors) and heterotrimeric guanine nucleotide-binding regulatory proteins (G proteins). G proteins are comprised of three subunits: a guanyl-nucleotide binding α subunit; a β subunit; and a γ subunit [for review, see Conklin, B. R and Bourne, H. R. (1993) Cell 73, 631–641]. G proteins cycle between two forms, depending on whether GDP or GTP is bound to the α subunit. When GDP is bound, the G protein exists as a heterotrimer, the Gαβγ complex. When GTP is bound, the α subunit disassociates, leaving a Gβγ complex. Importantly, when a Gαβγ complex operatively associates with an activated G protein coupled receptor in a cell membrane, the rate of exchange of GTP for bound GDP is increased and, hence, the rate of disassociation of the bound Gα subunit from the Gβγ complex increases. The free Gα subunit and Gβγ complex are capable of transmitting a signal to downstream elements of a variety of signal transduction pathways. This fundamental scheme of events forms the basis for a multiplicity of different cell signaling phenomena. For additional review, see H. G. Dohlman, J. Thorner, M. Caron, and R. J. Lefkowitz, Ann. Rev. Biochem, 60, 653–688 (1991).

In plants, there is evidence that a number of plant signal transduction pathways, including red and blue light signaling (Warpeha et al., 1991; Romero and Lam, 1993; Neuhaus et al, 1993), K+ channel regulation of stomatal opening (Fairley-Grenot and Assmann, 1991; Li and Assmann, 1993; Armstrong and Blatt, 1995), and auxin signal transduction (Zaina et al., 1990) are regulated through G-protein intermediates. More specifically, in certain of these studies, red light-dependent responses in the tomato mutant aureus were measured after microinjection of either the GTP analogue GTPγS or cholera toxin, either of which cause constitutive activation of a G-protein, and were found to produce the same effects as microinjecting phytochrome and exposing the plant to red light. Injection of inhibitors GDPβS or pertussis toxin were effective in blocking red light-dependent responses.

It has also been suggested that an inhibitory G-protein modulates blue light-dependent K+ channel opening on the basis of electrophysiological studies using GTPγS, GDPβS and toxins. In separate experiments it was shown that blue light can activate a GTP-binding protein in the plasma membrane of peas. In rice, the binding of GTPγS to vesicles in vitro is increased by auxin, while binding of GTPγS decreased binding of auxin. This binding relationship suggests that auxin activation of a G-protein stimulates cell elongation. In addition, there is evidence for G-protein mediation of plant defense responses (Legendre et al., 1992, Vera-Estralla et al., 1994; Beffa et al., 1995).

Gα-like proteins, having molecular weights close to that of the animal Gα subunits and recognized by antibodies against animal Gα subunits, have been detected in a large number of plant species (for reviews see Ma, 1994 and Kaufman, 1994) and three genes encoding G protein-α subunits have been identified. The first was cloned from *Arabidopsis thaliana* (Ma et al. 1990) using PCR primers based on sequences known to be conserved between animal G protein α-subunits. The predicted protein has all of the consensus sequences for guanine nucleotide binding and hydrolysis that are characteristic of GTP-binding proteins and shows 36% identity with rat Gi(1-3) and bovine transducin. Using the *Arabidopsis thaliana* gene as a probe, genes were identified in both tomato (Ma et al., 1991) and soybean (Kim et al., 1995). The *Arabidopsis thaliana* tomato and soybean genes share over 80% identity, suggesting that plant G-protein α-subunits may be highly conserved. Both *Arabidopsis thaliana* and tomato DNA appear to have single genes based on Southern blot analysis, whereas multiple genes may be present in soybean. Single genes encoding G protein β subunits have also been cloned from maize and *Arabidopsis thaliana* (Weiss et al., 1994). The predicted protein sequences shares 76% identity with each other and 41% identity with mammalian G protein β subunits.

Although the sequence of the plant G α subunits have been conserved relative to that of the mammalian G α subunits, there is no published data that demonstrates that the function of the plant protein is also conserved. Although physiological studies implicate G protein mediated responses in a number of pathways based on sensitivity of the response to cholera or pertussis toxins or the enhancement of the GTP binding to membranes by specific stimuli, this evidence is indirect. Prior to the work as detailed herein, the art has failed to provide direct evidence that these effects occur by the same mechanism by which they occur in other systems. In fact, it has recently been reported by one of the leaders in the field of plant G-protein molecular biology, that it is " . . . unlikely that the plant G αs are functional homologues of any of the non-plant ones." . . . (ibid. Hong Ma 1994).

Protein-mediated signaling systems are present in organisms as divergent as yeast, plant, and man. The yeast *Saccharomyces cerevisiae* is utilized as a model eukaryotic organism. Due to the ease with which one can manipulate the genetic constitution of the yeast *Saccharomyces cerevisiae,* researchers have developed a detailed understanding of many complex biological pathways. It has been demonstrated in numerous systems that the evolutionary conservation of protein structure is such that many heterologous proteins can substitute for their yeast equivalents. For example, mammalian Gα proteins can form heterotrimeric complexes with yeast Gβγ proteins [Kang, Y.-S., Kane, J., Kuijan, J., Stadel, J. M., and Tipper, D. J. (1990) Mol. Cell. Biol. 10, 2582–2590]. Screening assays utilizing yeast strains genetically modified to accommodate functional expression of plant G proteins offer significant advantages in research involving the identification of plant proteins that function in intracellular signaling systems, such as G-protein coupled systems.

SUMMARY OF THE INVENTION

A first aspect of the present invention is directed to a method of identifying a plant protein that functions in an intracellular signaling system such as a G protein coupled cellular signaling system. This is accomplished by providing a host cell with a nucleotide sequence encoding the plant protein it is desired to identify, which may be a plant protein suspected of being or functioning in a manner similar to a G protein subunit or a plant protein that is suspected of being or functioning in a manner similar to a G protein coupled receptor that functions in the intracellular signaling systems of mammals, insects (such as mammalian G protein coupled systems and insect G protein coupled systems), and the like. In certain preferred embodiments, an endogenous corollary component of a G protein coupled cellular signaling pathway, such as a Gα protein subunit, is rendered inoperative in the host cell. The host cell is transformed with a nucleotide sequence encoding the plant protein it is desired to identify and analyze, and the transformed host cell is allowed to grow under suitable conditions. The presence or absence, and sometimes the degree of said growth, is measured as an indication that the plant protein it is desired to identify has restored growth to said host cell, in the absence of its endogenous counterpart. From this information, it is determined that the target protein under study functions in a G-protein coupled cellular signaling system. In some cases, depending on the target under study, the protein may function in a "G protein subunit-like" manner, and particularly in the manner of a Gα subunit. G Protein components other than Gα may be rendered inoperative to identify and analyze various other components of G protein coupled systems, or intracellular systems that function as G-protein coupled systems. For example, the target protein may function as another G protein component such as a Gβ or γ component or a Gβγ complex. And in yet other preferred embodiments of the method of the invention, the plant protein it is desired to identify is suspected of being or functioning in a manner similar to a G protein coupled receptor. In such embodiments, the endogenous receptor or receptor-like protein is rendered inoperative or is removed entirely. The target protein of interest is introduced, and thus, in either event, the host cell is transformed with a nucleotide sequence that encodes a G-protein-coupled receptor-like protein.

In each of the above embodiments, all or a portion of the endogenous G protein signaling pathway may optimally be rendered inoperative and replaced with counterpart plant proteins, such as a Gα subunit, Gβ subunit, and the like, or chimeric constructs containing a portion of the host cell derived subunit fused to a plant derived portion.

A second aspect of the present invention is directed to expression vectors and host cells transformed with the aforementioned target plant protein it is desired to identify. In certain preferred embodiments, the host cell contains a first heterologous nucleotide sequence which encodes a protein of interest, which is suspected of being a protein component that functions in an intracellular system, such as a G protein coupled cellular signaling system. Such nucleotide sequence may encode a G protein-coupled receptor protein, a G protein subunit, or a plant protein that is suspected of functioning in a manner analogous to a G protein coupled receptor or G protein subunit. In certain preferred embodiments, the nucleotide sequence encodes all or a portion of a G protein (such as an α, β, or γ subunit), wherein the G subunit is plant-derived, at least in part. Various chimeric and trimeric hybrid G protein constructs are within the contemplation of the present invention. For example, in certain other embodiments, all or a portion of a nucleotide sequence encoding a heterologous plant G protein α subunit is fused to a nucleotide sequence from a yeast G protein or a mammalian G protein α subunit. Also within the contemplation of the expression vectors and host cells described herein are those transformed with a first heterologous nucleotide sequence which encodes a protein suspected of being a G protein coupled receptor-like protein and a second nucleotide sequence which encodes all or a portion of plant derived G protein subunit, as described above. In the most preferred embodiments, the expression system is yeast, and the expression vectors and transformed cells may usefully contain a third heterologous nucleotide sequence comprising a pheromone-responsive promoter and an indicator gene positioned downstream from the pheromone-responsive promoter and operatively associated therewith.

The vectors and cells utilizing the preferred yeast expression system may further contain several mutations effective to disconnect the pheromone responsive signal transduction pathway of the endogenous yeast host cell from that host cell's natural cell cycle arrest pathway, or to otherwise increase sensitivity of the response of the cell to activation. In certain preferred embodiments, wherein a yeast cell is the host cell, these mutations include 1) a mutation of the yeast SCG1/GPA1 gene, which inactivates the yeast Gα protein, facilitating interaction of the heterologous plant protein with the G protein; 2) a mutation of a yeast gene to inactivate its function and enable the yeast cell to continue growing in spite of activation of the pheromone response signal transduction pathway, preferred embodiments being mutations of the FAR1 and/or FUS3 genes; and, 3) a mutation of a yeast gene, the effect of which is to greatly increase the sensitivity of the response of the cell to receptor-dependent activation of the pheromone response signal transduction pathway, preferred genes in this regard being the SST2, STE50, SGV1, STE2, STE3, PIK1, AFRI, MSG5, and SIG1 genes.

A third aspect of the present invention is chimeric expression constructs and host cells transformed therewith comprising a first nucleotide sequence encoding a plant protein suspected of functioning in a G protein coupled cellular signaling pathway, and further comprising in operative association therewith, a second nucleotide sequence which encodes an endogenous non-plant protein of the host cell or functional heterologous equivalent, which would be the corollary G protein component. Such constructs and cells may also contain a third heterologous nucleotide sequence comprising a pheromone-responsive promoter and an indicator gene positioned downstream from the pheromone-responsive promoter and operatively associated therewith. When the host cell is a yeast cell, the constructs and cells may further contain the mutations discussed above.

A productive signal is detected in a bioassay through coupling of the transformed heterologous protein to the host cell's signal transduction pathway.

A fourth aspect of the present invention is a method of assaying compounds to determine effects of ligand binding to heterologous plant receptors by measuring effects on cell growth. In certain preferred embodiments, host cells are cultured in appropriate growth medium to cause expression of heterologous plant proteins, which become dispersed in a liquid medium or embedded in a solid phase medium, such as agar, and then exposed to substances applied to the surface of the vesicles or plates containing same. Effects on the growth of cells are expected around substances that activate the heterologous plant protein and the signal transduction pathway. Increased growth may be observed with substances that act as agonists, while decreased growth may be observed with those that act as antagonists.

The term "G protein coupled cellular signaling system" as used herein refers to intracellular signaling systems that perform an intracellular signaling function similar to the well-known mammalian G protein-coupled receptor systems as discussed herein in the Background of the Invention, and display some of the structural hallmarks of such a system. The terms "Gα-like, Gβ-like, Gγ-like, and Gγβ-like complex" inter alia, are intended to include mutants and homologs thereof and encompass proteins that function in a G protein coupled cellular signaling system, or equivalent intracellular signaling system in a manner analogous to the well-studied mammalian systems.

The term "chimeric" as used herein generally refers to a protein expressed by a recombinant nucleotide sequence that is made by joining separate fragments of nucleotide sequences from more than one organism or species, or from more than one gene of the same organism or species. The term is used interchangably with fusion protein or construct and hybrid protein or construct and is not meant to limit such chimerics to those obtained solely through recombinant processes, it being understood that there may be other means of constructing same. "Trimeric" refers specifically to a construct comprising three such separate protein portions.

The term "heterologous" as used herein with respect to a host cell and nucleotide sequence expression constructs and techniques, refers to nucleotide sequences, proteins, and other materials originating from organisms other than that particular host cell. Thus, mammalian, avian, amphibian, insect, plant, and yeast should all be considered heterologous to one another.

The term "mammalian" as used herein refers to any mammalian species (e.g. human, mouse, rat, and monkey).

The term "nucleotide sequence" is meant to include all forms of linear polymers comprising nucleotide bases, without limitation, including when appropriate, DNA, genomic DNA, cDNA, RNA, synthetic oligonucleotides, and the like.

The terms "receptor" or "receptor-like" as used herein are interchangeable and intended to encompass proteins that are identified as receptors or that function as a receptor and are further intended to include subtypes of proteins, and mutants and homologs hereof, along with the nucleotide sequences encoding same. One skilled in the art will also understand that in some instances, it may not be necessary that the entire receptor be expressed to achieve the purposes desired. Accordingly, the term receptor is meant to include truncated and other variant forms of a given receptor, without limitation.

The term "upstream" and "downstream" are used herein to refer to the direction of transcription and translation, with a sequence being transcribed or translated prior to another sequence being referred to as "upstream" of the latter.

In the method and constructs of the present invention, a host cell is transformed with a nucleotide sequence encoding a target plant protein it is desired to identify, characterize, and/or analyze. Any plant protein that is suspected of functioning in a G protein-coupled cellular signaling system or the like, such as a G protein coupled receptor, a protein that functions in a manner similar to G protein coupled receptors in intracelluar signaling, or portions thereof, as well as the plant G protein subunits themselves or proteins suspected of being such subunits or like components may be identified and assayed in accordance with the identification method and constructs of the present invention.

In certain embodiments of the methods of the invention, it is desirable to render inoperative all or a portion of the host cell's endogenous G protein coupled cellular signaling pathway. This may be accomplished through any of a variety of means, such as by deletion of the endogenous gene suspected of being an integral component in such signaling pathway, disruption of such endogenous gene by insertion of a foreign DNA sequence, and expression of an antisense G protein gene, to name but a few techniques. In certain embodiments, the endogenous G protein-coupled pathway component that is rendered inoperative may be replaced with a corresponding plant G protein-coupled pathway component, or a hybrid construct containing all or a portion of a host cell's endogenous component, or its functional equivalent from such heterologous system, fused to such plant protein. Any DNA sequence which codes for a plant G subunit may be used to prepare the constructs of the invention, or even a protein suspected of functioning as such a plant G protein subunit. Examples of such plant proteins include, but are not limited to, *Arabidopsis thaliana* G protein α subunit, *Arabidopsis thaliana* G protein β subunit, tomato G protein α subunit, soybean G protein α subunit, maize G protein β subunit, as further discussed in the Ma et al. (17–19) and Kim et al. (13) publications as listed on the attached Bibliography.

One skilled in the art will understand from the teachings as presented herein that the G proteins useful in the constructs and yeast cells of the present invention may comprise plant Gα subunits, or chimeric plant/mammalian Gα subunits, yeast/plant Gα subunits, or trimeric yeast/mammalian/plant versions. One can determine which configuration is best suited for adequate coupling to a cellular signaling system by simply constructing vectors as taught herein, transforming host cells, and determining the presence or absence of continued growth. Depending on the assay indicator system utilized, continued growth of said host cell is generally an indication that the G protein construct is functioning in said host cell in place of the functional endogenous G protein coupled cellular signaling complex. In certain preferred embodiments, the G protein α subunit is the plant subunit of choice, and especially that derived from *Arabidopsis thaliana*.

Certain chimeric G protein constructs may also provide enhanced signal transduction with regard to particular heterologous receptors. One skilled in the art may prepare useful chimeric constructs by fusing operative regions of intracellular signaling components. Such operative regions may be selected in accordance with the teachings in this art. For example, the sites of interaction between Gα subunits and Gβγ subunit complexes or G protein-coupled receptors have been described (for review see B. R. Conklin and H. R. Bourne, 1993 (3)). The sites of interaction between Gα subunit complexes and the Gβγ subunits have been mapped to the amino terminus of the G protein α subunit, and possibly to the hα2 (α2 helix) and i1 (insert sequence 1) regions of the protein. The carboxy terminus of the G protein α subunit contains the region of the protein for which the strongest evidence for interaction with the G protein coupled receptor exists. Other regions that may contain contact points include the amino terminus and the G5 region (the G regions are peptide sequences that are conserved in all GTPases). A chimeric G protein alpha subunit with enhanced interaction with the yeast G protein βγ complex may thus be constructed by fusing the amino terminus of the yeast G protein α subunit containing these Gβγ contact sites with the carboxy terminus of the plant G protein α subunit.

Any DNA sequence which codes for a Gβ subunit or a Gγ subunit or other such subunits, or other components that interact with a plant Gα may be used to practice the present invention, including the host cell's endogenous components. G proteins and subunits useful for practicing the present invention include subtypes, and mutants and homologs thereof, along with the nucleotide sequences encoding same. The host cells may express endogenous Gβ and/or Gγ, a Gβγ complex, or appropriate plant counterpart subunits, or may optionally be engineered to express heterologous Gβ and/or Gγ (e.g., mammalian, plant, or various combinations thereof) in the same manner as they would be engineered to express heterologous Gα (see reference 22).

Heterologous nucleotide sequences are expressed in a host by means of an expression "construct" or "vector." An expression vector is a replicable nucleotide construct in which a nucleotide sequence encoding the protein of interest is operably linked to suitable control sequences capable of affecting the expression of a protein or protein subunit coded for by the nucleotide sequence in the intended host. Examples of cloning vector systems that may be utilized to obtain and/or amplify plasmids encoding the proteins it is desired to express include, but are not limited to, microorganisms such as bacteria transformed with recombinant bacteriophage DNA; plasmid DNA or cosmid DNA expression vectors. Host-expression systems useful for expression of the proteins it is desired to express include yeast carrying the recombinant yeast expression vectors containing the coding sequence; insect cell systems infected with recombinant virus expression vectors (e.g., baculovirus) containing the coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence or a nucleic acid containing the coding sequence; or animal cell systems infected with recombinant virus expression vectors (e.g., adenovirus, vaccinia virus) or containing stably integrated nucleotide sequences. Vectors useful for practicing the present invention include plasmids, viruses (including bacteriophage), and integratable DNA fragments (i.e., fragments integratable into the host genome by genetic recombination). The vector may replicate and function independently of the host genome, as in the case of a plasmid, or may integrate into the genome itself, as in the case of an integratable DNA fragment.

Generally, suitable control systems capable of affecting the expression of the protein of interest are selected in accordance with the vector/host system utilized, and are in operable association with the nucleotide sequence it is desired to express. Eukaryotic control sequences generally include a transcriptional promoter. However, it may also be appropriate that a sequence encoding suitable mRNA ribosomal binding sites be provided, and (optionally) sequences which control the termination of transcription. DNA regions are operably associated when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading frame.

In addition, a promoter operable in a host cell is one which binds the RNA polymerase of that cell, and a ribosomal binding site operable in a host cell is one which binds the endogenous ribosomes of that cell. Suitable vectors may in some instances also contain replicon control sequences (when the vector is non-integrating) which are derived from species compatible with the intended expression host.

The above-mentioned expression elements of these systems vary in their strength and specificities. Thus, depending on the host/vector system utilized, any of a number of suitable transcription and translation elements, including constitutive and inducible promoters, may be used in the expression vector. For example, when cloning in bacterial systems, promoters such as pL of bacteriophage λ, plac, ptrp, ptac (ptrp-lac hybrid promoter) and the like may be used.

In cases where plant expression vectors are used, the expression of the coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, biolistics, microinjection, electroporation, etc. For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9.

When cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the DNA SV40-, BPV- and EBV-based vectors may be used with an appropriate selectable marker. In cases where an adenovirus is used as an expression vector, the coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the protein in infected hosts. (E.g., See Logan & Shenk, 1984, Proc. Natl. Acad. Sci. (USA) 81:3655–3659). Alternatively, the vaccinia 7.5K promoter may be used. (E.g., see Mackett et al., 1982, Proc. Natl. Acad. Sci. (USA) 79:7415–7419; Mackett et al., 1984, J. Virol. 49:857–864; Panicali et al., 1982, Proc. Natl. Acad. Sci. 79:4927–4931).

An alternative expression system which could be used to express the protein of interest is an insect system. In one such system, *Autographa californica* nuclear polyhedrosis virus (AcNPV) is used as a vector to express foreign genes. The virus grows in *Spodoptera frugiperda* cells. The coding sequence may be cloned into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (E.g., see Smith et al., 1983, J. Viol. 46:584; Smith, U.S. Pat. No. 4,215,051).

Specific initiation signals may also be required for efficient translation of inserted coding sequences. These signals include the ATG initiation codon and adjacent sequences. In some cases where the entire gene encoding the protein of interest, including its own initiation codon and adjacent sequences, is inserted into the appropriate expression vector, no additional translational control signals may be needed. In other cases it may be necessary to modify these sequences to optimize the expression of a heterologous gene in a host system. However, in cases where only a portion of the coding sequence is inserted, exogenous translational control signals, including the ATG initiation codon, must be provided. Furthermore, the initiation codon must be in phase with the reading frame of the coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., 1987, Methods in Enzymol. 153:516–544).

Transformed host cells of the present invention are cells which have been transformed or transfected with the vectors constructed using recombinant DNA techniques or other suitable methodology, and express the protein or protein subunit coded for by the heterologous DNA sequences. The vectors and methods disclosed herein are suitable for use in host cells over a wide range of prokaryotic and eukaryotic organisms. Methods which are well known to those skilled in the art can be used to construct expression vectors containing the nucleotide sequence it is desired to express and appropriate transcriptional/translational control signals. These methods include in vitro recombinant DNA techniques and in vivo recombination/genetic recombination (see Maniatis et al., 1989, Molecular Cloning—A Laboratory Manual, Cold Spring Harbor Laboratory, N.Y.). In the case of yeast cells, the vectors can also be introduced by mating cells with yeast of the opposite mating type that carry the vector. By utilizing techniques well known in the art in conjunction with the teachings as set forth herein, one skilled in the art may select the optimal host cell/vector expression system to express and identify the desired target plant proteins. In addition, a host cell strain may be chosen which modulates the expression of the inserted sequences, or modifies and processes the gene product in the specific fashion desired. Such modifications and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, and the like.

Following the introduction of foreign DNA, engineered cells are allowed to grow under suitable growth conditions. For example, the cells may undergo a selective culturing protocol. The selectable marker in the recombinant plasmid confers resistance to the selection and allows transformed cells to grow to form colonies or foci, which in turn can be cloned and expanded into cell lines. The growth is measured. Growth generally indicates that the target plant protein functions in the intracellular signaling system while the absence of growth generally indicates that it does not. The degree of growth may also be assessed and extrapolated to the effectiveness of the target plant protein as an intracellular signaling component or to determine its function in the intracellular signaling machinery. This method may advantageously be used to engineer cell lines which express the plant protein, and which respond to mediated signal transduction, such as G protein coupled signaling systems. Detailed methodologies for selective culturing protocols suitable for use with a variety host cell expression systems may be found in *Current Protocols in Molecular Biology* [4].

An example of the numerous selection systems that may be used, include but are not limited to, the herpes simplex virus thymidine kinase (Wigler, et al., 1977, Cell 11:223), hypoxanhine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk, hgprt or aprt cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes. Recently, additional selectable marker genes have been described, namely trpB, which allows cells to utilize indole in place of tryptophan; hisD, which allows cells to utilize histinol in place of histidine ([Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

Recombinant yeast expression systems are particularly useful in the practice of the present invention, and are therefore preferred for use herein. A variety of yeast cultures, and suitable expression vectors for transforming yeast cells, are known. See e.g., U.S. Pat. Nos. 4,745,057; 4,797,359; 4,615,974; 4,880,734; 4,711,844; and 4,865,989. *Saccharomyces cerevisiae* is the most commonly used among the yeasts, although a number of other yeast species are commonly available, such as *Schizosaccharomyces pombe*, and the like. See. also, U.S. Pat. No. 4,806,472 (*Kluveromyces lactis* and expression vectors therefore); 4,855,231 (*Pichia pastoris* and expression vectors therefore). In certain embodiments, yeast vectors may contain an origin of replication from the endogenous 2 micron yeast plasmid or an autonomously replicating sequence (ARS) which confers on the plasmid the ability to replicate at high copy number in the yeast cell, centromeric (CEN) sequences which limit the ability of the plasmid to replicate at only low copy number in the yeast cell, a promoter, DNA encoding the heterologous DNA sequences, sequences for polyadenylation and transcription termination, and a selectable marker gene. Exemplary plasmids and detailed materials and methods for making and using same are provided in the EXAMPLES section.

Any promoter capable of functioning in yeast systems may be selected for use in the preferred expression constructs and host cells of the present invention. Suitable promoting sequences in yeast vectors include the promoters for metallothionein, 3-phosphoglycerate kinase (PGK) [Hitzeman et al., (1980) J. Biol. Chem. 255, 2073] or other glycolytic enzymes [(Hess et al., (1968) J. Adv. Enzyme Reg. 7, 149; and Holland et al., (1978) Biochemistry 17, 4900], such as enolase, glyceraldehyde-3-phosphate dehydrogenase, hexokinase, pyruvate, decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657. Other promoters, which have the additional advantage of transcription controlled by growth conditions, are the promoter regions for alcohol dehydrogenase, 1,2,-isocytochrome C, acid phosphates, degradative enzymes associated with nitrogen metabolism, and the aforementioned metallothionein and glyceraldehyde-3-phosphate dehydrogenase, as well as enzymes responsible for maltose and galactose utilization, such as the galactose inducible promoter, GAL1. Particularly preferred for use herein are the PGK, GAL1, and alcohol dehydrogenase (ADH) promoters. Finally, in constructing suitable expression plasmids, the tennination sequences associated with these genes may also be ligated into the expression vector 3' of the heterologous coding sequences to provide polyadenylation and termination of the mRNA. In preparing the preferred expression vectors of the present invention, translational initiation sites are chosen to confer the most efficient expression of a given nucleic acid sequence in the yeast cell [see Cigan, M. and T. F. Donahue 1987, GENE, Volume 59, pp. 1–18, for a description of suitable translational initiation sites]. A particularly preferred nucleotide expression vector useful for carrying out the present invention comprises such an aforementioned promoter sequence, positioned upstream to the translational initiation site of the heterologous nucleotide sequence encoding for the plant protein it is desired to express. Particularly preferred promoters in this regard are the GAL1, PGK, and ADH promoters.

Any of a variety of means for detecting the effects of the transduced plant protein on a G protein coupled cellular signaling system of the host cell may be utilized. For example, measurement of the disassociation of G$\alpha$ from G$\beta\gamma$ can be made through conventional mechanical disruption techniques. However, detectable biological responses may also lend themselves to measurement. One such biological response is the activation of the pheromone induced mating signal transduction pathway, which is the preferred method of detecting the effects in the assay systems herein presented, the basic premise of which is discussed in more detail in PCT 95/21925. As set forth therein, selected mutations in endogenous yeast genes can lead to hypersensitivity to pheromone and an inability to adapt to the presence of pheromone. For example, introduction of mutations that interfere with function into yeast strains expressing the target proteins enables the development of extremely sensitive bioassays for the effect of the target protein, or for the effect of substances that interact with G protein coupled receptors. Other mutations e.g. STE50, sgvl, ste2, ste3, pik1, msg5, sig1, and afr1, have the similar effect of increasing the sensitivity of the bioassay. One skilled in the art will understand that increased sensitivity of the assay systems is attained through a variety of mutations, such as deletion of one or more of these aforementioned genes, introduction of nucleotide substitutions that disrupt the activity of the protein, introduction of mutations that down-regulate their expression, or in certain instances, effecting their overexpression. For example, in the STE50 construct, overexpression of the gene is desired, not deletion of the gene. Thus, introduction of a constellation of mutations in the mating signal transduction pathway results in a yeast cell well suited to expression of plant proteins, which are able to functionally respond in an intracellular signaling system.

In conjunction with one or more of the above-referenced mutations, a particularly convenient method for detecting the effects of the plant protein on the cellular signaling system is to utilize a conventional genetic indicator system. Thus, in certain preferred embodiments, the cells are provided with an additional heterologous nucleotide sequence, comprising a pheromone-responsive promoter and an indicator gene positioned downstream from the pheromone-responsive promoter and operatively associated therewith. With such a sequence in place, the detecting step can be carried out by monitoring the expression of the indicator gene in the cell. Any of a variety of pheromone responsive promoters could be used, examples being promoters driving any of the aforementioned pheromone responsive genes (e.g. mF$\alpha$1, mF$\alpha$2, MFA1, MFA2, STE6, STE13), the BAR1 gene promoter, and the FUS1 gene promoter. Likewise, any of a broad variety of indicator genes could be used, with examples including the HIS3, G418r, URA3, LYS2, CAN1, CYH2, and LacZ genes. A particularly preferred reporter gene construct is utilized by fusing transcription control elements of a FUS1 gene to HIS3 protein coding sequences, and replacing the original FUS1 gene with this reporter construct. Expression of the HIS3 gene product is thereby placed under the control of the pheromone signal transduction pathway. Yeast strains (his3) bearing this construct are able to grow poorly on supplemented minimal medium lacking histidine, and are sensitive to an inhibitor of the HIS3 gene product. Activation of gene expression results in increased growth on this medium. In other preferred embodiments, plasmids carry a FUS1-lacZ gene fusion. Expression of these gene fusions is stimulated in response to receptor activation by binding of pheromone. Therefore, signal transduction can be quantitated by measuring β-galactosidase activity generated from the FUS1-lacZ reporter gene, or detection of enhanced growth on minimal media in yeast expressing the FUS1-HIS3 reporter gene.

Other useful reporter gene constructs, still under the control of elements of the pheromone signal transduction pathway, but alternative to the above-discussed reporter systems, may involve signals transduced through other heterologous effector proteins that are coexpressed. For example, 1) stimulation of a heterologous adenylylcyclase may permit a yeast strain lacking its own adenylylcyclase due to mutation in the cdc35 gene to survive, 2) stimulation of a heterologous G protein-coupled potassium channel may permit a yeast strain unable to grow in medium containing low potassium concentration [(trk1, trk2), for example, see Anderson, J. A. et al (1992)( Proc. Natl. Adad. Sci. USA 89, 3736–3740] to survive, or 3) stimulation of a heterologous PLC-β may permit a yeast strain lacking its own PLC [(plc)], for example, see Payne, W. E. and Fitzgerald-Hayes, M. (1993) Mol. Cell Biol. 13,4351–4363] to survive.

Any DNA sequence which codes for an adenylylcyclase may be used to practice the present invention. Examples of adenylylcyclase include the product of the D. melanogaster Rutabaga gene and the mammalian subunit types I-VIII [for review see, Tang, W. -J. and Gilman, A. G. (1992) Cell 70, 869–872], and mutants and homologs thereof, along with the DNA sequences encoding same, which are useful for practicing the present invention.

Any DNA sequence which codes for a G protein-gated potassium channel may be used to practice the present invention. Examples of G protein-coupled potassium channel include GIRK1 [Kubo, Y. Reuveny, E., Slesinger, P. A., Jan, Y. N., and Jan, L. Y. (1992) Nature 365, 802–806], subunits useful for practicing the present invention, and mutants and homologs thereof, along with the DNA sequences encoding same.

Any DNA sequence which codes for a phospholipase protein may be used to practice the present invention.

Examples of phospholipase proteins include the D. melanogaster norpA gene product and the PLC-β proteins [for review, see Rhee, S. G., and Choi, K. D. (1992) J. Biol. Chem. 267, 12392–12396], subunits useful for practicing the present invention, and mutants and homologs thereof, along with the DNA sequences encoding same.

Transformed host cells of the present invention express the proteins or protein subunits coded for by the heterologous DNA sequences. When expressed, the plant protein is capable of functional interaction with the other G proteins of the intracellular signaling system. The G protein coupled receptors and some effectors, such as adenylyl cyclases and ion channels, are integral membrane proteins. The plant protein may also be associated with the membrane, as is the case with G proteins or the effector cGMP phosphodiesterase, or may be a membrane lipid, such as the phosophatidylinositol-phopholipases. Some of the G protein in the cell may be concentrated on intracellular membranes including the endoplasmic reticulum, golgi complex, endosomes and secretory vesicles (F. A. Barr et al., 1992).

Implementation of the methods and constructs described herein will facilitate description of structural and functional aspects of receptor-ligand and receptor-G protein interactions. The role of plant proteins that modify the response of receptors and G proteins may be worked out in detail with the assistance of this powerful genetic system. Importantly, the system provides a generalized approach to the study of the functioning and identification of components of the G protein coupled transduction system in plants, as well as a generalized approach to screening assays utilizing the G protein coupled signal transduction system. Once the plant intracellular signaling system is better understood, any of a variety of pesticides, herbicides, fungicides and the like may be designed, having novel mechanisms of action. The present invention provides expression constructs and assay systems adapted to receive any of a variety of plant proteins it is desired to identify, in the form of "expression cassettes". The plant protein it is desired to study is simply inserted into the vectors herein provided, and expressed in appropriate host cells. The systems presented herein also facilitate the identification of ligands for plant G protein-coupled proteins. In certain assay embodiments of the invention, any of a variety of substances may be contacted with a host cell expressing the target plant protein, to ascertain the effect of such substance on the intracellular signaling system. Such substances may comprise organic compounds, metal ions, peptides, proteins and the like, depending on the needs of the user. Suitable assay parameters, such as length of interaction, media utilized, and other test conditions are constructed in accordance with techniques generally utilized in the art.

The following Examples are provided to further illustrate various aspects of the present invention. They are not to be construed as limiting the invention.

EXAMPLE 1

To determine whether the function of the plant G protein α subunit is conserved compared with yeast and mammalian proteins we tested the ability of the plant G-protein α subunit to complement the growth defect in a yeast strain that is unable to grow because of a mutation in the endogenous yeast SCG1 gene. In *Saccharomyces cerevisiae* the mating pathway is regulated through two seven-transmembrane receptors, Ste2 and Ste3, and a trimeric G-protein intermediate. In the absense of mating pheromone, the G protein α-subunit, Scg1, forms a complex with the βγ-subunits. This association represses the activity of the βγ subunits so that the cell continues to divide. Binding of the mating pheromones a-factor and α-factor to the STE2 and STE3 receptors, respectively, results in the dissociation of the G-protein subunits, activation of the mating pathway and growth arrest.

Haploid yeast cells deficient for the endogenous G protein α subunit do not divide because the mating pathway is constitutively activated. The mammalian G-protein α subunits Gαs (Dietzel, C. and J. Kurgen. 1987 Cell), Gαi2 and Gα0 (Kang et al., Mol. Cell Bio., 1990) are able to complement this growth defect in scg1 mutant yeast strains and restore the ability of the cells to divide by repressing the activity of the yeast βγ subunits. In these studies, a cDNA encoding the plant G protein α subunit (GPα1) expressed in yeast was able to form a finctional complex with the yeast G protein βγ subunits, and restore growth.

Materials and Methods

Cloning of GPA1 gene The gene was cloned from a λYES Arabidopsis cDNA library (S. Ellide et al.) by designing probes based on the published sequence of the gene (H. Ma et al.). The library was screened under stringent conditions with $P^{32}$-labeled DNA fragments as described (Current Protocols 4) and a total 32 positive clones were identified out of 300,000 plaques. Four of these were purified. To obtain a plasmid capable of replication in yeast and *E. coli*, phage DNA was isolated (Qiagen) and digested with NotI, which releases the plasmid carrying the inserted Arabidopsis cDNA, and religated. The plasmids recovered by this technique (pAC525 and pAC526) are similar to the ones that are recovered by site-specific recombination between the lox sequences flanking the plasmid within the lambda phage sequence, except that there is a duplication of the lox recombination site. The identity of the clones was verified by restriction digestion and sequence analysis. The two full length GPA1 clones that were recovered from the library and used in these experiments differ in length at the 3' end. pAC525 is oriented so that it can be transcribed from the *E. coli* lac promoter and pAC526 is oriented so that it can be transcribed from the yeast GAL1-10 promoter. pAC527 was constructed by removing the GPA1 cDNA insert from pAC525 by digestion with EcoRI and religating the isolated cDNA fragment with pYES. Clones were screened to identify a plasmid in which the cDNA insert could be transcribed from the GAL1-10 promoter, and pAC527 was identified.

Alteration of the 5' end and introduction into different vectors. The two GPA1 cDNAs were cloned as SalI-EcoRI fragments into pGEM3Z to remove the Arabidopsis 5' end. The plasmids were digested with PstI/SalI and a double-stranded oligonucleotide was inserted to reconstruct the Arabidopsis coding sequence and replace the 5' noncoding sequence with a polyadenine sequence that is favored for translation initiation in yeast. The GPA1 cDNAs with modified 5' ends were cloned into pGK and pYES as EcoRI fragments. The oligonucleotides used in this cloning procedure were: 5' GAATTCAAAAAATGGGCTTACTCTG-CAGTAGAAG 3' (SEQ ID NO:1) and 5' TCGACTTC-TACTGCAGAGTAACCCATTTTTTGAATTCCTGCA 3' (SEQ ID NO:2). The second oligonucleotide has overhangs for PstI and SalI restriction sites.

Yeast strains, transformations, media The diploid *Saccharomyces cerevisiae* strain used in these studies was LY19 (Matox/Mata, ade2-101, his3-Δ200, leu2-Δ1, lys2-801, trp1-Δ63, ura3-52, GPA1/gpa1Δ::HIS), a derivative of YPH501 (Stratagene). Halo assay controls were strains Y280(a) and Y281(α). Transformants expressing the Arabidopsis GPA1 gene under the control of the GAL1-10 promoter (pAC1003 and pAC1005) were grown in YEP supplemented with 2% galactose to induce gene expression, transformants expressing the GPA1 gene under the control of the PGK promoter (pAC572 and pAC573) were grown in YEP supplemented with 2% glucose. Yeast tetrads were plated on SC-ura supplemented with 0.1% 5-fluoro orotic acid to select for the growth of yeast that lost the plasmid expressing the plant GPA1 gene.

Transformation of yeast Yeast were transformed using lithium acetate as described in Methods in Yeast Genetics (M. Rose et al., 1990).

Halo assays A single yeast colony was resuspended in 200 µl sterile water. One tenth (20 µl) was spread on half of a YPD plate, 20 µl of a 1:5 dilution was spread on the other half. Three filter discs were placed on each half, spotted with either 5 µl of water, 5 µl of 1 µg/µl α-factor or 5 µl of 2 µg/µl α-factor. Plates were incubated at 30° C. overnight.

Results

Complementation Assay

Two different sets of plasmids carrying the Arabidopsis GPA1 gene were introduced into a diploid yeast strain to perform complementation assays. pAC526 and pAC527 represent two independent cDNA clones that were isolated as phage from the Arabidopsis λYES cDNA library, and were subsequently converted to plasmids (see MATERIALS AND METHODS, supra). The GPA1 cDNA is expressed under the control of the yeast GAL1-10 promoter in this set of constructs. These clones contain approximately 200 base pairs of GPA1 5' noncoding sequence upstream of the translational start codon, and differ in the length of the polyA$^+$ tail. This plasmid is maintained in yeast in single copy due to the presence of a centromere. To obtain high-level expression of GPA1 in yeast, the coding regions were subdloned from pAC526 and pAC527 into pPGK to create pAC572 and pAC573. In this set of constructs the 5' non-coding region of the Arabidopsis GPA1 gene was removed and 5 adenine nucleotides were added upstream of the ATG start codon to optimize translation initiation in yeast. These are high copy plasmids in which the GPA1 cDNA is expressed from the constitutive PGK promoter. In addition, the GPA1 cDNAs, lacking the Arabidopsis 5' end but containing the adenine residues upstream of the ATG, were subcloned from pAC572 and pAC573 and cloned back into pλYES. In these single-copy plasmids, designated pAC1003 and pAC1005, the GPA1 cDNAs are expressed under the control of the GAL1-10 promoter.

Plasmids carrying the Arabidopsis cDNAs encoding the G-protein α subunit were introduced into a diploid yeast strain carrying one wild-type and one mutant copy of the yeast SCG1 gene, which encodes the yeast G-protein α subunit. This diploid strain has a wild-type growth phenotype because the yeast G-protein α subunit binds to the βγ subunits to negatively regulate the mating pathway. When the yeast cells undergo meiosis and four haploid spores are formed, two spores will carry the wild-type yeast gene and two will carry the mutant copy of the yeast gene; all spores carry the plasmid expressing the Arabidopsis G-protein α subunit. The two spores with the wild-type SCG1 gene form colonies, but the spores with the mutated scg1 gene grow only if the Arabidopsis protein is able to form a functional complex with the yeast G-protein βγ subunits and repress the mating pathway.

When the diploid yeast strain heterozygous at the SCG1 locus was transformed with the high copy plasmids pAC572 and pAC573, which carry the Arabidopsis GPA1 gene expressed under the control of the constitutive PGK promoter, four spore tetrads were recovered. In each tetrad, two of the colonies appeared smaller in size, most likely because the interaction between the Arabidopsis GPα1 and the yeast βγ subunits is weaker than normally occurs with the yeast Scg1 protein and results in only a partial repression of the mating pathway. Thus, the Arabidopsis Gpa1 protein, like the mammalian G protein α subunits, is able to form a functional complex with the yeast βγ subunits to repress their activity.

Transformation of the diploid with plasmids pAC1003 and pAC1005, in which the GPA1 gene with the modified 5' end is cloned into the centromeric λYES plasmid, resulted in the recovery of two, three and four spore tetrads. This result was consistant with the segregation of a centromeric plasmid into spores during meiosis. As described for tetrads carrying the plasmids pAC572 and pAC573, two large colonies were seen in each tetrad and these expressed the wild-type yeast Scg1 protein. However, the colonies dependent on GPα1 for growth were smaller than the corresponding colonies seen after dissection of diploids carrying pAC572 and pAC573. This difference in size is presumably because the GPA1 gene is carried on a single-copy, centromere-containing plasmid so that less protein is produced than in those colonies expressing the gene carried on high-copy plasmids.

Viability of Tetrads on 5-fluoroorotic Acid

The assumption that the two spores that formed smaller colonies in each tetrad are those that are dependent on the Arabidopsis GPα1 protein for growth was tested by determining which colonies from tetrads could grow following loss of the plasmid carrying the Arabidopsis GPA1 gene. In the complementation studies described above, the Arabidopsis GPA1 gene is carried on plasmids carrrying the wild-type URA3 gene that is used as a marker for transformation into yeast cells lacking a functional URA3 gene. Cells that have lost the plasmid carrying both the URA3 gene and the Arabidopsis GPA1 gene can be recovered by patching cells from tetrads onto media containing 5-fluoroorotic acid (5-FOA), a compound that is toxic to yeast cells that have a wild-type copy of the URA3 gene. The only cells that should grow on 5-FOA are those that have lost the plasmid carrying both the URA3 marker gene and the Arabidopsis GPA1 gene, and do not depend on the Arabidopsis gene for growth. The ability to grow on this media is expected to segregate 2:2, since two colonies from each tetrad carry the wild-type yeast SCG1 gene. In an experiment in which tetrads carrying plasmids pAC572 and pAC573 were patched onto media containing both 5-FOA and uracil, only two of the patches from each tetrad were able to grow on this media, demonstrating that they carry the wild-type copy of the yeast SCG1 gene. These patches corresponded to the two larger colonies in each tetrad.

Appearance of Scg1-yeast Cells Expressing GPA1

The different colony sizes seen in the tetrads most likely reflects a weaker interaction between the plant Gpα1 protein and the yeast βγ subunits than occurs with the yeast Scg1 protein. This weaker interaction mnight result in only a partial repression of the mating pathway, causing the cells to grow more slowly than wild-type yeast cells. Microscopic observation of yeast cells expressing the Arabidopsis Gpα1 protein provided evidence supporting this hypothesis. The appearence of these yeast cells was similar to the appearance of wild-type yeast cells that had been exposed to mating pheromone and had undergone cell cycle arrest. These cells had the characteristic "shmoo" morphology of cells in which the which the mating pathway had been activated, in the absense of exposure to α-factor. However, in contrast to wild-type cells exposed to α-factor, many of these cells contain irregularly shaped buds. This is consistant with the observation that cells carrying the Gpα1 protein continued to grow.

Halo Assays

Yeast cells expressing Gpα1 were also tested to determine whether mating pheromone can cause growth arrest. Once mating pheromone binds to the yeast receptor, growth arrest will occur only if a functional receptor-G protein α subunit interaction results in activation of the G-protein. Halo assays were performed by exposing cells to α-factor spotted on filter discs. Cells were plated at two different densities, and two different concentrations of α-factor were spotted on the filter discs. When wild-type yeast cells of the a mating type are exposed to α-factor, a zone of growth inhibition around the disc occurs because the α-factor binds to the receptor and the G protein α subunit is activated. A control using yeast cells of the α mating type showed uniform growth around the filters because they express the receptor that responds to α-factor , but not to α-factor .

Two independent yeast transformants of the a mating type expressing only the Arabidopsis G protein alpha subunit were tested in this assay. In this case, the growth around the discs spotted with α-factor was also uniform. Because growth arrest is not apparent, it is unlikely that the Arabidopsis G protein alpha subunit is able to couple functionally with the yeast receptor. Yeast cells of the a mating type expressing both the yeast and the plant G-protein α subunits showed a zone of reduced growth around the disc, consistent with the hypothesis that the yeast G protein α subunit is inactivated as a result of the mating pheromone, but the plant α subunit is not.

Disscussion

Previous studies of the *Arabidopsis thaliana* GPA1 gene demonstrated that it encodes a protein that contains all known consensus sequences for GTP binding proteins and has approximately 33% homology to previously identified G protein α subunits from other organisms, including mammals, Drosophila and yeast (Ma et al.). In spite of the sequence similarity, there is no evidence that the GPA1 gene encodes a protein that functions as part of a trimeric G protein complex. To address this issue the GPA1 gene was used for complementation studies in a yeast strain lacking the endogenous G protein α subunit. Because the absence of the G protein α subunit results in activation of the mating pathway and leads to growth arrest, it is possible to express the Arabidopsis GPA1 gene in this mutant strain and ask whether the plant protein is able to restore growth. The ability to restore growth is dependent on the ability of the GPα1 protein to form a complex with the βγ subunits that results in repression of their acitivity.

The GPA1 cDNA was transformed into a diploid yeast strain heterozygous for a mutation in the yeast SCG1 gene. Dissection of tetrads demonstrated that spores expressing only the Arabidopsis GPα1 protein were able to give rise to colonies. Because the 5' noncoding region of the Arabidopsis GPA1 gene has a number of small open reading frames that may interfere with translation of the protein in yeast the 5' end of the GPA1 gene was altered to incorporate a sequence that is used more efficiently for translation initiation by yeast. The results of the complementation assay demonstrated that the Arabidopsis G protein α subunit, like many of the animal α subunits that have been tested (see Kang et al., 1990), can form functional complexes with the yeast βγ subunits. Not only the structure, but the function of the plant G protein was highly conserved compared with those that have been well-characterized in other systems.

Halo assays were performed to determine whether there is a fuctional interaction between the Arabidopsis G protein cc a subunit and the yeast α-factor receptor. Exposure of yeast cells to α-factor resulted in activation of the G protein and growth arrest when the yeast G protein α subunit was present, but not when the Arabidopsis G protein α subunit was present. A zone of reduced growth was apparent around the filter disc spotted with α-factor when both proteins were expressed in the same cell. This result, together with those seen with yeast cells expressing either the yeast or plant G protein α subunits, indicates that the cells continue to divide because the plant α subunit continues to couple with the βγ subunits following inactivation of the yeast G protein α subunit. This result gives credence to the supposition that there is usually a high degree of specificity in the interaction between the alpha subunit and the receptor.

The slower growth of yeast cells complemented by Arabidopsis GPα1 compared with those expressing the yeast protein is most likely due to incomplete repression of the activity of the yeast βγ subunits by the Arabidopsis protein. This is supported by the observation that the growth rate of the complemented yeast was dependent on the copy number of the plasmid; colonies carrying the GPA1 gene on a centromeric plasmid grew more slowly than those carrying the gene on a high-copy 2μ plasmid.

EXAMPLE II

Cloning of Arabidopsis G Protein α Subunits

The following examples demonstrate approaches for cloning plant G protein α subunits by complementation in yeast.

1. A plant cDNA library in which cDNAs are expressed under the control of a yeast promoter is transformed into a diploid yeast strain that is heterozygous for a mutation in the endogenous SCG1 gene. This mutation is preferably a disruption of the gene that is created by deleting a fragment of the gene, and inserting into the deleted gene an essential marker gene. One of many genes ((LEU2, HIS3, URA3) may be selected, depending on both the genotype of the diploid yeast strain and the marker carried on the cDNA library plasmid. The important criteria is that the yeast strain is homozygous for the mutation in the endogenous gene, and that the gene is not the marker used for selection of transformants following introduction of the cDNA library into the strain. For example, the diploid strain could be his3/his3, the wild-type HIS3 gene could be inserted into the SCG1 gene and the cDNA library is cloned into a plasmid expressing the URA3 marker gene. The plant cDNA library is introduced into this strain and the transformants are selected. The diploids transformants are sporulated to produce haploid spores, and plated onto media lacking histidine. In order to grow on this medium, a haploid strain would have to carry the wild-type HIS3 gene, and therefore the disrupted copy of the endogenous SCG1 gene, and a plant gene encoding a functional G protein α subunit.

Because diploids would also grow on this media, it would be useful to include an additional marker that is used to either select against growth of the diploids or distinguish between haploids or diploids that grow. An appropriate diploid is heterozygous for cyclohexamide resistance. Because resistance is a recessive trait, diploids will not grow if cyclohexamide is included in the media, and only haploids carrying the resistant copy of the gene should grow.

2. A plant cDNA library in which the cDNAs are expressed under the control of a yeast promoter is transformed into a haploid yeast strain which has a mutation in the genomic copy of SCG1 gene and which carries a plasmid expressing the wild-type SCG1 under the control of an inducible promoter. The strain is maintained in the presence of the inducer to produce the yeast G protein α subunit prior to transformation. After introduction of a plant cDNA, library transformants expressing the plant cDNAs are selected by plating cells on media lacking the inducer. Only those cells expressing plant G protein α subunits should grow on this media.

3. This Example is similar to #2 above, except that the wild-type yeast SCG1 gene is carried on the plasmid that is also carrying a URA3 marker gene. After introduction of a plant cDNA library, transfonnants expressing the plant G protein α subunit are selected by plating cells on media containing 5-FOA. Since only those cells that have lost the wild-type URA3 gene can grow on this medium, this selects for the growth of those cells which are expressing a functional plant G protein α subunit and which have lost the plasmid expressing the yeast SCG1 gene.

EXAMPLE III

Cloning of a G Protein-Linked Receptor

Cloning of a G protein linked receptor in yeast is accomplished by first expressing the plant G protein α subunit in the yeast strain, or alternatively, a plant/yeast hybrid G protein α subunit, which may have a higher affinity for the yeast's endogenous βγ subunits. This couples a yeast response to activation of the plant receptor. Yeast strains as disclosed in PCT 95/21925 are suitable for the expression of mammalian G protein-linked receptors, and preferably a strain that carries a mutation in the FAR1 gene. Activation of the mating pathway does not lead to cell growth arrest due to the mutations in this strain. Instead, the FUS3 promoter, which is activated when the mating pathway is activated, is fused to a either a selectable marker gene, such as the wild-type HIS gene, or to a visible marker gene, such as lacZ. The plant cDNA library expressed under the control of a yeast promoter is introduced into this strain, and the strain is then plated on medium containing the ligand, or putative ligand, that activates the receptor that is being identified in the experiment. The yeast cells expressing a receptor that can couple with the plant G protein α subunit expressed in the parent strain are either the only cells able to grow (if the marker gene were an essential gene) or the only cells that appear pigmented in the presence of colorametric substrate for β-gal (e.g., blue in the presence of X-gal). This growth or coloration is dependent on the presence of the ligand in the medium.

BIBLIOGRAPHY

1. F. A. Barr, A. Leyte and W. B. Huttner (1992). Trimeric G proteins and vesicle formation. Trends in Cell Biology 2: 91–94.
2. Beffa, R., Szell, M. Meuwly, P., Pay, A., Vogeli-Lange, R., Metraux, J-P., Neuhaus, G., Meins, F. and Nagy, F. (1995). Cholera toxin elevates pathogen resistance and induces pathogenesis-related gene expression in tobacco. EMBO J. 14(23): 5753–5761.
3. Conklin, B. R. and Bounne, H. R. (1993) Structural elements of Gα subunits that interact with Gβγ, receptors, and effectors. Cell 73: 631–641.
4. *Current Protocols in Molecular Biology* (1992) ed. F. M. Ausubel, R. Brent, R. E. Kingston, D. D. Moore, J. G. Seidman, J. A. Smith, K. Struhl
5. Blumer, K. J., and Thorner, J. (1991) Receptor-G protein signaling in yeast. *Annu. Rev. Physiol.* 53, 37–57.
6. Dietzel, C., and Kurgen, J. (1987) The yeast SCG1 gene: a Gα-like protein implicated in the α- and α-factor response pathway. Cell 50, 1001–1010.
7. Elledge, S. J., Mulligan, J. T., Ramer, S. W., Spottswood, M., and Davis, R. W. (1991)
8. λYES: A multifunctional cDNA expression vector for the isolation of genes by complementation of yeast and *Escherichia coli* mutations. Proc. Natl. Acad. Sci., USA 88, 1731–1735.
9. Fairley-Grenot, G. K. and Assman, S. M. (1991) Evidence for G-protein regulation of inward postassium ion channel current in guard cells of fava bean. Plant Cell 3; 1037–1044.
10. Huang, H., Weiss, C. A., and Ma., H. (1994). Regulated expression of the Arabidopsis G protein α subunit gene GPA1 Int. J. Plant Sci. 155, 3–14.
11. Kang, Y., Kane. J., Kujan., J., Stadel,. J. M., and Tipper, D. J. (1990) Effects of expression of mammalian Gα and hybrid mammalian-yeast Gα proteins on the yeast pheromone response signal transduction pathway. Mol. Cell Bio. 10(6), 2582–2590.
12. Kaufman, L. S. (1994). GTB-binding signaling proteins in higher plants J. Photochem. Photobiol. B. Biol. 22:3–7.
13. Kim, W. Y., Cheong, N. E., Lee, D. C., Je, D. Y., Bahk, J., D., Cho, M. J. and Lee, S., Y. (1995) Plant Physiol. 108: 1315–1316.
14. King, K., Dohlman, H. G., Thorner, J., Caron, M. G., and Lefkowitz, R. J. (1990) Control of yeast mating signal transduction by a manmalian $β_2$-adrenergic receptor and $G_s$ α subunit.
15. Legendre, L., Heinstein, P. F. and Low, P. S. (1992) Evidence for participation of GTP-binding proteins in elicitation of the rapid oxidative burst in cultured soybean cells. J. B. C. 267: 20140–20147.
16. Li, W. and Assmann, S. M. (1993) Characterization of G-protein regulated outward K+ current in mesophyll cells of *Vicia faba*. P.N.A.S. USA 90: 262–266.
17. Ma., H., Yanofsky, M. F., and Meyerowitz, E. M. (1990). Molecular cloning and characterization of GPA1, a G protein α subunit gene from *Arabidopsis thaliana*. Proc. Natl. Acad. Sci., USA 87, 3821–3825.
18. Ma., H., Yanofsky, M. F., and Huang, H. (1991). Isolation and sequence analysis of TGA1 cDNAs encoding a tomato G protein α subunit. Gene 107, 189–195.
19. Ma, H. (1994) GTP -binding proteins in plants: new members of an old family. Plant Mol. Biol. 26: 1611–1636.
20. Neuhaus, G., Bowler, C. Kern, R. and Chua, N.-H. (1993) Calcium/calmodulin-dependent and -independent phytochrome signal transduction pathways. Cell 73: 937–952.
21. Romero, L. C. and Lam, E. (1993) Guanine nucleotide binding protein involvement in early steps of phytochrome-regulated gene expression. P.N.A.S. USA 90:1465–1469.
22. Rose, M., Winston, F. and Hieter, P. (1990) Methods in Yeast Genetics. Cold Spring Harbor Laboratory Press.
23. Ryba, N. J. P., Findlay, J. B. C., and Reid, J. D. (1993) The molecular cloning of the squid (Loligo foresi) visual Gq-α subunit and its expression in *Saccharomyces cerevisiae*. Biochem. J. 292,333–341.
24. Vera-Estrella, R., Barkla, B. J., Higgins, V. J. and Blumwald, E. (1994) Plant defense response to fungal pathogens. Plant Physiol. 104: 209–215.
25. Warpeha, K. M. F., Hamm, H. E., Rasenick, M. M. and Kaufman, L. S. (1991) A blue-light activated GTP-binding protein in the plasma membranes of etiolated peas. P.N.A.S. USA 88: 8925–8929.
26. Weiss, C. A., Huang, H., and Ma., H. (1993). Immunolocalization of the G protein α subunit encoded by the GPA1 gene in Arabidopsis. The Plant Cell 5, 1513–1528.
27. Weiss, C. A., Garnaat, C. W., Mukai, K., Hu, Y. and Ma, H. (1994). Isolation of cDNAs encoding guanine nucleotide-binding protein B-subunit homologues from maize (ZGB1) and Arabidopsis (AGB1). Proc. Natl. Acad. Sci. USA 91: 9554–9558.
28. Zaina, S., Reggiani, R. and Bertani, A. (1990) Preliminary evidence for involvement of GTP-binding proteins in auxin signal transduction in rice (*Oryza savita* L.) coleoptile. J. Plant Physiol. 136:653–658.

What is claimed is:

1. A transformed host cell comprising an inoperative component of a G protein subunit complex and a nucleotide sequence that codes for a heterologous plant G protein, wherein the heterologous plant G protein finctions as a component of the G protein subunit complex in the host cell.

2. The transformed host cell of claim 1, wherein said G protein subunit complex is selected from the group consisting of plant G protein, chimeric mammalian/plant G protein, yeast/plant G protein, and trimeric yeast/plant/mammalian G protein.

3. The transformed host cell of claim 1, wherein said nucleotide sequence codes for a plant Gα protein.

4. The transformed host cell of claim 1, claim 2 or claim 3 wherein the host cell is a yeast cell.

\* \* \* \* \*